United States Patent [19]

Gault

[11] 4,242,672
[45] Dec. 30, 1980

[54] PATIENT MONITORING SYSTEM AND SWITCH

[76] Inventor: Robert L. Gault, 140 Gilman St., Garden City, Mich. 48135

[21] Appl. No.: 849,809

[22] Filed: Nov. 9, 1977

[51] Int. Cl.³ .............................................. G08B 21/00
[52] U.S. Cl. ................................... 340/573; 340/514; 340/530; 340/636; 340/667
[58] Field of Search ............... 340/573, 667, 530, 514, 340/636, 516, 524, 525

[56] References Cited

U.S. PATENT DOCUMENTS

| Re. 28,754 | 3/1976 | Cook et al. ............................ 340/573 |
| Re. 28,915 | 7/1976 | Ogden et al. ......................... 340/514 |
| 2,818,477 | 12/1957 | Gollhofer . |
| 3,325,799 | 6/1967 | Farris . |
| 3,439,358 | 4/1969 | Salmons . |
| 3,533,095 | 10/1970 | Collins . |
| 3,534,350 | 10/1970 | Sellinger et al. ...................... 340/514 |
| 3,582,692 | 6/1971 | Palini . |
| 3,760,794 | 9/1973 | Basham ................................ 340/573 |
| 3,781,843 | 12/1973 | Harrison et al. . |
| 3,836,900 | 9/1974 | Mansfield . |
| 3,991,414 | 11/1976 | Moran . |
| 4,019,112 | 4/1977 | Satoh .................................. 340/636 |
| 4,020,482 | 4/1977 | Feldl . |
| 4,139,846 | 2/1979 | Conforti ............................... 340/636 |

Primary Examiner—Glen R. Swann, III

[57] ABSTRACT

A switch is placed on a bed, chair, or other object and is maintained in closed condition so long as a patient occupies the bed, chair, or other object and continues to exert sufficient weight on the switch. When the weight acting on the switch is relieved, the switch opens to cause an associated circuit to give an immediate audible alarm. The circuit also causes a visible alarm to be given shortly thereafter. The circuit is powered by a D.C. battery and includes a low voltage monitor which causes the audible alarm only to be given when the battery voltage drops below a certain level indicative of the need to replace the battery. A three position control switch establishes off, on, and test modes of operation. The patient monitoring switch comprises a tape switch arranged in a T-shape configuration, and the switch is foldable in half for use with a chair.

9 Claims, 4 Drawing Figures

PATIENT MONITORING SYSTEM AND SWITCH

BACKGROUND OF THE INVENTION

This invention pertains to a patient monitoring system and switch for providing alarm signals to indicate that the patient has left an object which he has been occupying such as a bed, chair, or like object.

There are various types of patient monitoring systems and switches which have heretofore been proposed. An ensuing section of this application entitled "Prior Art Statement" discusses selected types which were developed as a result of a novelty search conducted in connection with the present invention. A principal purpose of certain patient monitoring systems is to provide an alarm signal to attending personnel that the patient is in danger of falling from or has just left the object which he has been occupying. The systems are frequently used where the patient is in such a physical state that the attending personnel should be immediately summoned if the patient is in such imminent danger of falling from or has just left the object.

The present invention provides an improved patient monitoring system and switch. One feature of the system is that both audible and visible alarm signals are given, with the audible alarm being immediately given and with the visible alarm being given shortly thereafter. In this manner the audible alarm may be momentarily given without the visible alarm being given. However, should the audible alarm be given longer than just momentarily, then the visible alarm is given. Once the visible alarm has been given it continues until reset by attending personnel, even though the audible alarm may be terminated earlier by the return of the patient to the proper position. Uniquely constructed electronic solid state circuitry implements this feature. The circuitry includes a three position control switch for establishing off, on, and test modes of operation. The system is powered by a D.C. battery, and the circuitry includes a low voltage monitor which causes the audible alarm only to be given when the battery voltage drops below a critical level indicative of the need to replace the battery. The circuitry is designed, however, to remain operative over a limited range of battery voltage below the critical level thereby affording a certain time to replace the battery before the visible system fails for lack of power. Another feature of the invention relates to the patient monitoring switch itself. The switch has a generally planar configuration for placement on a bed, preferably between the mattress and the spring. The switching element itself is a tape switch which is arranged in a T-shape configuration whose overall dimensions are generally coextensive with the overall dimensions of the planar configuration. The switch is foldable in half from its planar configuration so that it may be placed on a smaller object of patient occupancy, such as the seat of a chair.

The foregoing features, along with additional features, advantages, and benefits of the invention, become more apparent in the ensuing description and accompanying drawings which disclose the invention in detail. A preferred embodiment is disclosed in accordance with the best mode presently contemplated in carrying out the invention. The subject matter in which an exclusive property is claimed is set forth in each of the numbered claims at the conclusion of the description, and such subject matter is considered patentable over the prior art of which applicant is aware, as set forth in the following Prior Art Statement.

Prior Art Statement

A novelty search performed in connection with the present invention developed the following U.S. Pat. Nos. 2,818,477; 3,325,799; 3,439,358; 3,533,095; 3,582,692; 3,715,541; 3,781,843; 3,836,900; 3,961,201; 3,991,414; 4,020,482; and Re28,754.

U.S. Pat. No. 2,818,477 discloses a monitor switch comprising a pair of sections connected by resilient means. Each section supports one of the switch contacts, and the resilient means, when the switch is in the free position, holds the two sections at an obtuse angle slightly less than a straight angle so that the switch contacts are closed. When disposed under an occupied bed, the sections are placed in a planar configuration to open the switch contacts. When the bed is unoccupied, the switch assumes its free position to close the contacts and cause an audible alarm to be given.

U.S. Pat. No. 3,325,799 discloses a respiration monitor using strain gauges and a circuit for giving an audible or visible alarm.

U.S. Pat. No. 3,439,358 discloses a sensor for a bed or chair using radiated high frequency electrical signals.

U.S. Pat. No. 3,533,095 discloses a horse mattress with a pneumatic pressure actuated switch which gives simultaneous audible and visible alarms.

U.S. Pat. No. 3,582,692 discloses a UJT in an alarm circuit.

U.S. Pat. No. 3,715,541 discloses a specific type of tape switch in an automobile seat.

U.S. Pat. No. 3,781,843 discloses a pneumatic type switch.

U.S. Pat. No. 3,836,900 discloses a mattress material with resilient resistive material in a respiration monitor.

U.S. Pat. No. 3,961,201 discloses a tape switch installation in a bed frame wherein the switch contacts close to actuate a circuit which causes the simultaneous occurrence of a visible alarm at the patient's room and an audible alarm at the nurse's station.

U.S. Pat. No. 3,991,414 discloses a wire actuated switch which operates a warning light at an attendant's station.

U.S. Pat. No. 4,020,482 discloses another pneumatic type switch.

U.S. Pat. RE No. 28,754 discloses a system providing an audible alarm, which may be time delayed from switch actuation, and contains a circuit having a UJT and associated RC timing circuit.

This Prior Art Statement is furnished in compliance with applicant's duty of disclosure as defined in the Patent and Trademark Office Rules for patent cases.

DESCRIPTION OF THE PREFERRED EMBODIMENT

Figure 1:
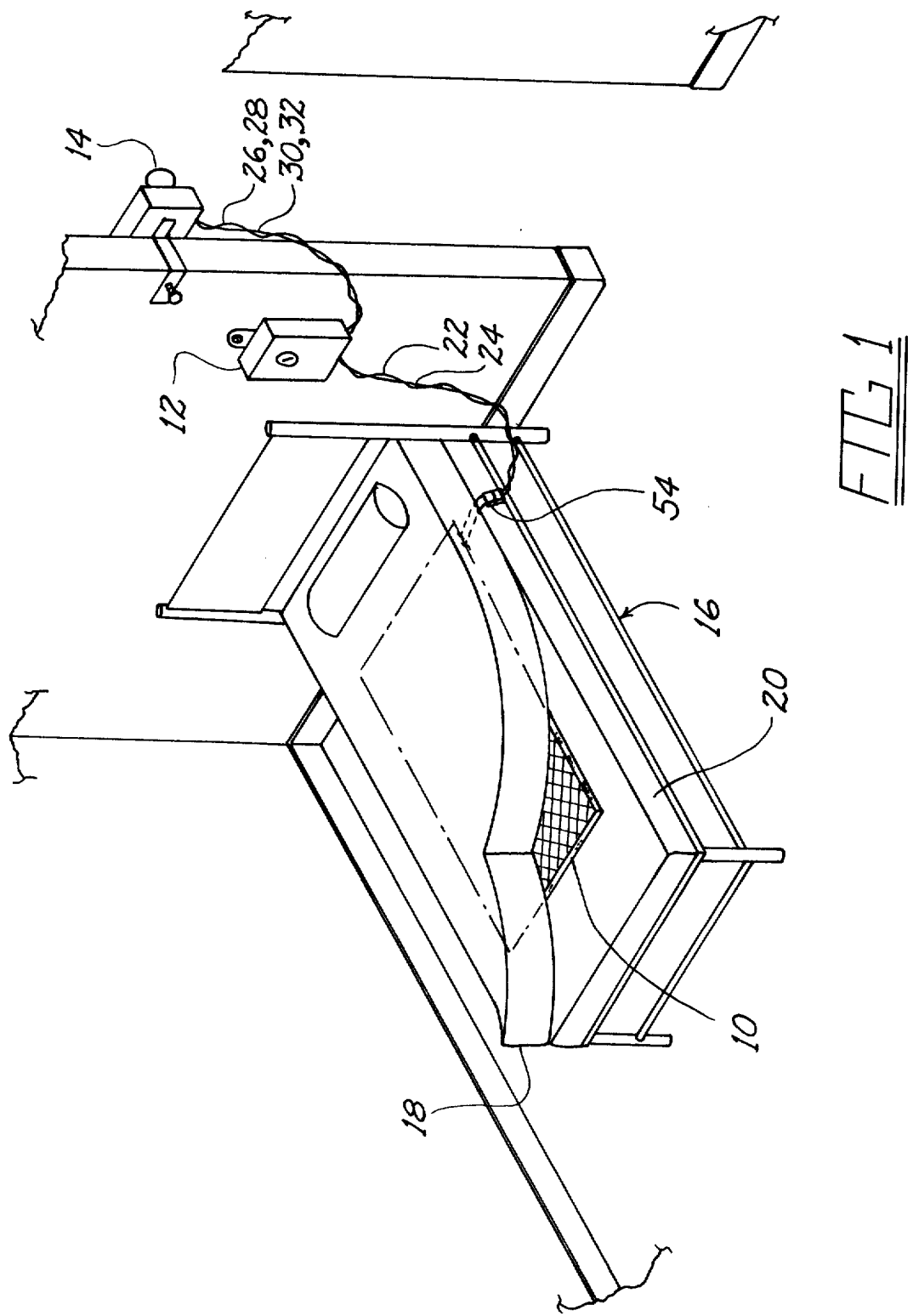
FIG. 1 is a perspective view illustrating an exemplary system embodying principles of the present invention.

The patient monitoring system of the present invention is shown in FIG. 1 and includes a patient monitoring switch 10, a control unit 12, and an alarm unit 14. The switch 10 is disposed in association with a bed 16 to sense patient occupancy thereof, being placed between the mattress 18 and the bed spring 20. When the bed is occupied, the switch is closed and when the bed is unoccupied, the switch is open. The switch is connected with control unit 12 by a pair of wires 22, 24. Control unit 12 may be conveniently placed near the bed, for example being hung on the wall near the bed as shown. The control unit contains the electrical circuitry which will be hereinafter described including a control switch. The control unit is connected to the alarm unit 14 by the four wires 26, 28, 30, 32. The alarm unit may be conveniently mounted outside the patient's room adjacent the doorway as shown. Briefly, the system is turned on by attending personnel with the patient in the bed. Should the patient leave the bed for any reason (i.e., getting up intentionally or falling out accidentally), switch 10 will be actuated to in turn actuate alarm unit 14 via control unit 12.

Figure 2:
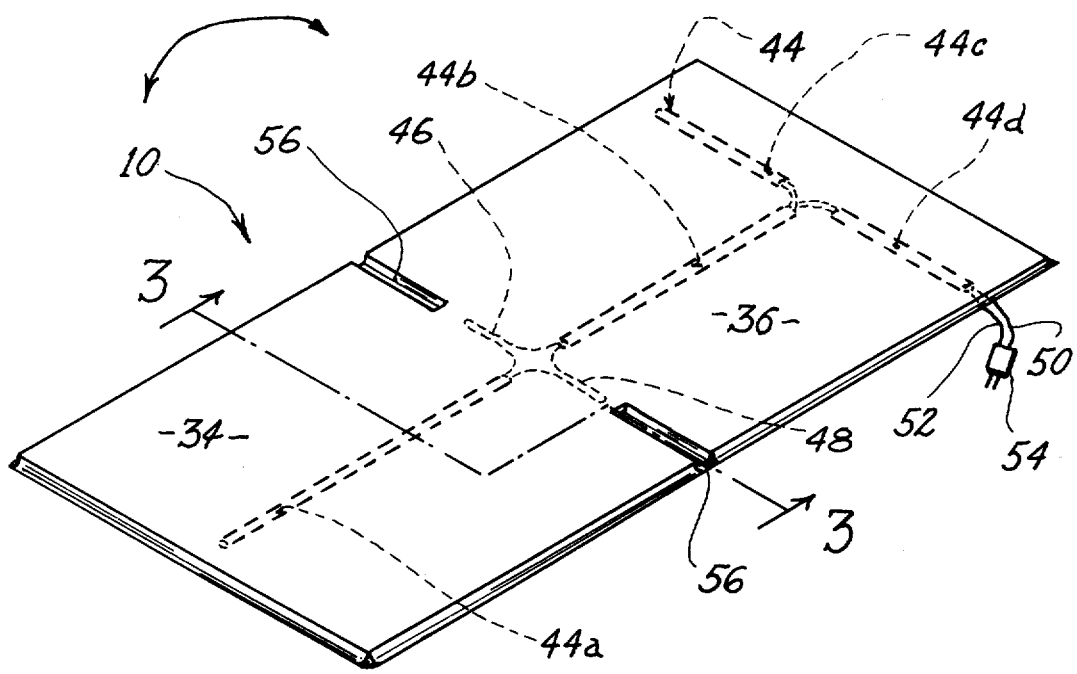
FIG. 2 is a perspective view of the patient monitoring switch used in the system of FIG. 1.
Figure 3:
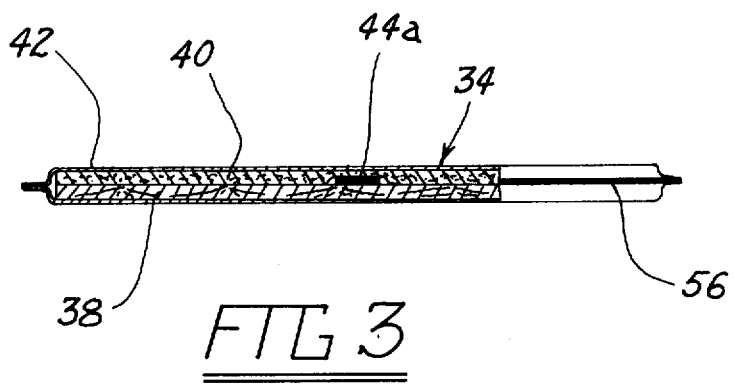
FIG. 3 is a sectional view taken in the direction of arrows 3—3 in FIG. 2.

Switch 10, which is believed novel by itself, is disclosed in detail in FIGS. 2 and 3. As shown in FIG. 2, switch 10 has a generally planar configuration and when in this configuration is intended to be used with a bed, as in FIG. 1. As will be seen however, the switch may be placed in a different configuration for use with a smaller object such as a chair seat. When in the configuration shown in FIG. 2, switch 10 is seen to comprise two halves 34, 36 of essentially identical size. By way of example only, each half may be about eighteen inches square so that the switch has overall dimensions of about eighteen inches by thirty-six inches when in the configuration of FIG. 2. Each half 34, 36 comprises a sturdy supporting section 38, preferably a composition board or the like. A pad 40, such as a fiber or plastic foam pad, is disposed to overlie each supporting section 38. The switch is enclosed by a cover 42, such as a flexible plastic, like vinyl. The switching element of switch 10 is a tape switch 44 arranged in a T-shape configuration and having overall dimensions generally coextensive with the dimensions of the planar configuration of the switch as shown in FIG. 2. The tape switch 44 may be fabricated from four segments 44a, 44b, 44c, 44d of conventional tape switch structure. The conventional tape switch structure has a pair of spaced conductors forming an open circuit when in the free state. When the tape switch structure is compressed by a force acting thereon, the spaced conductors make contact to form a closed circuit. In switch 10 the lower half of the T-shape is provided in half 34 by the tape switch segment 44a while the upper half of the T-shape is provided in half 36 by the remaining three segments 44b, 44c, 44d. Corresponding conductors of the two segments 44a, 44b are electrically joined by the wires 46, 48. Segments 44b, 44c, 44d are similarly electrically joined at their junction by additional wires. Switch 10 includes the wires 50, 52 leading from tape switch 44 to provide for connection in circuit, for example via a connector plug 54 to the wires 22, 24. The tape switch segments are disposed between the composition boards and the pads and may be held in place by any suitable means. For example they may be held by separate fasteners on the boards or adhered by suitable cement. Importantly, the T-shape arrangement is advantageous in obtaining an early indication of the patient being in danger of falling from or actually leaving the bed. For particular example, assume the patient gets up from the supine position and sits on the side of the bed. By disposing the top of the T-shape toward the head of the patient with switch 10 disposed generally beneath the patient's torso, the switch will open as the patient comes to the sitting position thereby providing an alarm even before the patient has actually left the bed. Switch 10 is endowed with the further capability of use with smaller objects such as chairs. The two halves 34, 36 may be folded onto each other for such usage. Such folding capability is imparted by providing suitable clearance between the two composition boards and pads. The top and bottom of cover 42 may be joined as at 56 to define the folding line. The wires 46, 48 are looped as indicated to allow for the folding and to avoid overflexing the wires. Thus, switch 10 is particularly advantageous for monitoring patient occupancy of an object such as a bed or chair.

Figure 4:
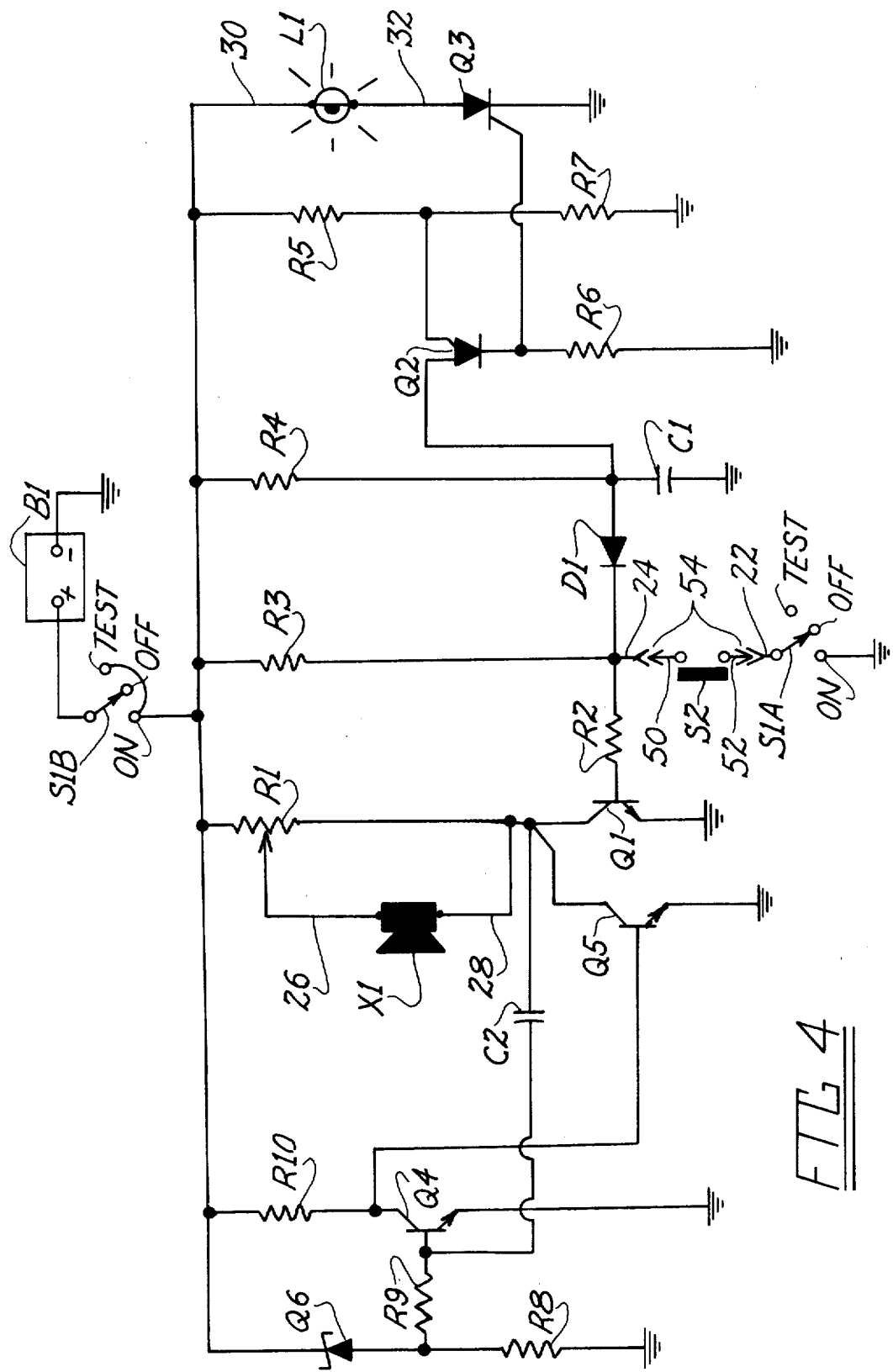
FIG. 4 is an electrical schematic diagram of circuitry used in the system of FIG. 1.

FIG. 4 illustrates the electrical circuitry of the system. The contacts designated S2 represent the contacts of switch 10. An audible alarm is designated by the reference X1 and a visible alarm by the reference L1. Both alarms are contained in unit 14. The remaining circuitry is housed in control unit 12. Power is supplied by a D.C. battery B1, and a control switch having two sets of contacts S1A, S1B is selectively operable to one, off and test positions for establishing the operating mode of the system.

When the control switch is placed in the off position, battery B1 is disconnected from the circuit and the system will not operate due to lack of power. When the control switch is placed in the on position, the battery is connected to power the circuit; also switch S2 is connected in circuit. Thus, in on position, the circuit is under the control of the patient monitoring switch. When the control is placed in test, switch contacts S2 are not in circuit, but the battery is connected to power the circuit.

Let it be assumed that the control switch is in the on position. So long as the patient occupies the bed, the switch contacts S2 remain closed. This causes a ground signal to be applied through the resistor R2 to the base of the NPN transistor Q1 to prevent the transistor from conducting. Because audible alarm X1 is in series with the collector-emitter of transistor Q1, the audible alarm will not be energized by current from the battery so long as switch contacts S2 remain closed. Should the contacts now open to indicate that the patient has left the bed, the ground is removed from the base of transistor Q1. Now current can flow from the positive battery terminal through resistors R3 and R2 to the base of transistor Q1 causing the transistor to conduct. Therefore, current also flows from the positive battery terminal through alarm X1 and the collector-emitter of transistor Q1 causing the audible alarm to be immediately given. The potentiometer R1 provides for adjustment of the intensity of the audible alarm signal and is preferably adjusted by a screwdriver type adjustment which will minimize the likelihood of unauthorized individuals tampering with the intensity of the audible alarm signal. Thus, it will be appreciated that the audible alarm is immediately given, upon the patient monitoring switch opening. When the switch again closes, it will be apparent that transistor Q1 is again rendered non-conductive to terminate the audible alarm.

The visible alarm L1 is also controlled by switch contacts S2 but the visible alarm signal is delayed slightly from the time at which contacts S2 open, for example about a two second delay. Light L1 is connected in series across the battery by the anode-cathode circuit of the SCR (silicon controlled rectifier) Q3. So long as the contacts S2 remain closed, SCR Q3 remains non-conductive and the light L1 is not illuminated. The closed condition of contacts S2 serves to prevent the capacitor C1 from being charged, the ground signal being conducted through the contacts S2 and the diode D1 to the junction of the resistor R4 and capacitor C1. The voltage across capacitor C1 is applied to the anode of the UJT (unijunction transistor) Q2. A reference voltage is applied to the gate of the UJT via the voltage divider composed of resistors R5 and R7. When contacts S2 open, capacitor C1 charges through resistor R4. When the transient reaches a level sufficient to fire the UJT, a pulse is delivered across the resistor R6 to the gate-cathode of SCR Q3 causing the SCR to conduct thereby lighting the visible alarm L1. The circuit parameters are selected so that a two second delay ensues between the opening of contacts S2 and the lighting of light L1. It is important to observe that contacts S2 must remain open during the delay period for the visible alarm to be given. Should contacts S2 close before the light is illuminated, the charge on capacitor C1 is almost instantly drained via diode D1 and contacts S2 to ground. This means that the delay period must be restarted from the beginning when contacts S2 once again open.

A low voltage monitor serves to monitor the battery voltage and to cause the audible alarm only to be given when the battery voltage drops below a predetermined critical level. The circuitry is designed, however, to permit the alarm to be operative over a limited voltage range below this critical level affording a limited time to replace the old battery with a fresh one without loss of visible alarm capability. The low voltage monitor includes a zener diode Q6 and resistor R8 connected in series across the battery. So long as the battery voltage remains above the critical level, the zener diode is conductive. With the zener diode conductive, transistor Q4 is held conductive and transistor Q4 holds transistor Q5 non-conductive. As the battery voltage passes through the critical level, the zener diode becomes less conductive. Transistor Q4 likewise becomes less conductive and transistor Q5 becomes more conductive. The conduction of transistor Q5 activates the audible alarm X1. The visible alarm is unaffected and will respond only to switch contacts S2. The purpose of the capacitor C2 is to provide a feedback connection whereby the audible alarm will be intermittently given when a low voltage condition occurs.

The design of the circuit and selection of component values minimizes power consumption by the unit, promoting a long shelf life and maximum intervals between replacement of batteries. By way of example, a circuit using the following values has been constructed and successfully operated.

B1—+9VDC
C1—5MFD
C2—33MFD
D1—1N4001
L1—14VDC
Q1—2N4124
Q2—2N6027
Q3—C106
Q4—2N3563
Q5—2N3563
Q6—4.3V Zener
R1—10 KOHMS
R2—100 KOHMS
R3—47 KOHMS
R4—500 KOHMS
R5—150 KOHMS
R6—22 OHMS
R7—220 KOHMS
R8—8.2 KOHMS
R9—5.6 KOHMS
R10—2.2 KOHMS
X1—SC628 "Sonalert"

In summary, the invention provides a new and unique patient monitor system and switch which offers improved advantages and benefits. The system is operated by the attending personnel activating the system when the patient is in bed. With the patient in bed switch contacts S2 are closed. The control switch is operated from off to test. In test, transistor Q1 immediately becomes conductive by current flow through resistors R3 and R2 and the audible alarm sounds. Capacitor C1 is permitted to charge (because S1A is open), and the visible alarm is therefore given shortly after the audible alarm (about two seconds). This proves that the system is operational. The control switch is then placed in on position. Because the switch must pass through the off position in going from test position to on position, SCR Q3 is switched off and the lamp L1 is extinguished. This guarantees that there must be a two second delay before the visible alarm can once again be given when next the audible alarm sounds. By making the control switch key-actuated, unauthorized tampering with the control switch is avoided. When switch contacts S2 open, the alarms are given in the manner explained above. With the two second delay, momentary openings of switch 10 by the patient shifting in bed will not light the lamp. However, when the lamp is lighted, it cannot be extinguished by subsequent closure of switch contacts S2, but rather requires resetting of the control by use of the key switch. Thus, it requires the attending personnel to investigate.

What I claim is new is:

1. Patient monitoring apparatus for signaling patient egress from an object of patient occupancy, such as a bed, chair, or the like, comprising:

switch means associated with said object selectively operable to a first state when said object is occupied and to a second state when said object is unoccupied;

an audible alarm for providing an audible alarm signal;

a visual alarm for providing a visual alarm signal; and circuit means operatively coupling said switch means and said audible alarm and visual alarm effective to cause said audible alarm to give said audible alarm signal when said switch means is in its second state and to not give said audible alarm signal when said switch means is in its first state, and including time delay circuit means effective to cause said visual alarm signal to be given in predetermined time delayed relationship to the operation of said switch means to its second state from its first state only if said switch means is continuously maintained in its second state for the duration of the predetermined time delay, said circuit means being further effective to cause said visual alarm to continue giving said visual alarm signal independent of subsequent operation of said switch means back to its first state.

2. Patient monitoring apparatus as set forth in claim 1 wherein an SCR is connected in series with said visual alarm across a DC source of energizing potential and said SCR is triggered by said time delay circuit means after the predetermined time delay to cause said visual alarm to be energized by said DC source and give the visual alarm signal, said time delay circuit means comprising a UJT and associated RC circuit wherein said RC circuit is caused to execute a timing transient from an initial condition in response to operation of said switch means from its first state to its second state and said UJT is triggered by a predetermined level of the transient relative to said initial condition to in turn trigger said SCR.

3. Patient monitoring apparatus as set forth in claim 2 wherein a diode operatively connects said RC circuit and said switch means and is so poled as to permit execution of said transient so long as said switch means is in its second state and to restore said RC circuit to said initial condition in response to operation of said switch means to its first state.

4. Patient monitoring apparatus as set forth in claim 1 wherein said time delay circuit means includes an RC timing circuit which is caused to execute a timing transient from an initial condition when said switch means is operated to said second state and including diode means operatively connecting said RC timing circuit and said switch means and so poled as to permit execution of the timing transient so long as said switch means is in its second state and to restore said RC circuit to said initial condition in response to operation of said switch means to its first state.

5. Patient monitoring apparatus as set forth in claim 1 wherein said audible alarm and said visual alarm are contained in a unit, said object is disposed in a room having a doorway, and said unit is disposed outside of said room adjacent said doorway.

6. Patient monitoring apparatus as set forth in claim 1 wherein said circuit means and said audible alarm and said visual alarm are powered by a DC battery and including means for monitoring the voltage of said battery effective to cause said audible alarm to give said audible alarm signal when the battery voltage drops below a predetermined potential, but not to cause said visual alarm to give said visual alarm signal.

7. Patient monitoring apparatus for signaling patient egress from an object of patient occupancy, such as a bed, chair, or the like, comprising:

switch means associated with said object selectively operable to a first state when said object is occupied and to a second state when said object is unoccupied;

a first type of alarm means for providing a first type of alarm signal;

a second type of alarm means for providing a second type of alarm signal which is different from said first type of alarm signal;

circuit means operatively coupling said switch means and said two types of alarm means effective to cause said first type of alarm means to give said first type of alarm signal when said switch means is in its second state and to not give said first type of alarm signal when said switch means is in its first state, and to cause said second type of alarm means to give said second type of alarm signal when said switch means is operated to its second state from its first state and remains in its second state for a predetermined length of time, and to continue giving said second type of alarm signal independent of subsequent operation of said switch means back to its first state;

a three position control switch selectively operable to off, on, and test positions and operably connected to said switch means and said circuit means for preventing said switch means from causing said two types of alarm signals to be given when said control switch is in off position, for permitting said switch means to control said two types of alarm means when said control switch is in on position, and for causing said two types of alarm signals to be given when in test position independent of the condition of said switch means; and said three position control switch having the off position intermediate the test and on positions and said circuit means and said control switch being so arranged that after said control switch has been operated to the test position to cause both said alarm signals to be given, the transition through the off position during subsequent operation to the on position causes said second alarm signal to be terminated for a minimum of a predetermined time delay period after said control switch is in the on position independent of the condition of said switch means.

8. Patient monitoring apparatus as set forth in claim 7 wherein said three position control switch is a key-actuated switch.

9. Patient monitoring apparatus as set forth in claim 7 wherein said control switch has two sets of contacts, one set for operatively associating said circuit means with a source of DC energizing potential, the other set for operatively associating said switch means with said circuit means.

* * * * *